(12) United States Patent  
Kraemer

(10) Patent No.: US 9,414,832 B2  
(45) Date of Patent: Aug. 16, 2016

(54) APPARATUS AND METHOD FOR SECURING THE STOMACH TO THE DIAPHRAGM FOR USE, FOR EXAMPLE, IN TREATING HIATAL HERNIAS AND GASTROESOPHAGEAL REFLUX DISEASE

(75) Inventor: Stefan J. M. Kraemer, Seattle, WA (US)

(73) Assignee: EndoGastric Solutions, Inc., Redmond, WA (US)

( * ) Notice: Subject to any disclaimer, the term of this patent is extended or adjusted under 35 U.S.C. 154(b) by 0 days.

(21) Appl. No.: 12/660,367

(22) Filed: Feb. 24, 2010

(65) Prior Publication Data

US 2010/0168507 A1    Jul. 1, 2010

Related U.S. Application Data

(62) Division of application No. 11/203,680, filed on Aug. 12, 2005, now abandoned.

(51) Int. Cl.
*A61F 2/02* (2006.01)
*A61B 17/04* (2006.01)
(Continued)

(52) U.S. Cl.
CPC ......... *A61B 17/0401* (2013.01); *A61B 17/0469* (2013.01); *A61B 17/1114* (2013.01); *A61B 17/29* (2013.01); *A61B 2017/003* (2013.01); *A61B 2017/00292* (2013.01); *A61B 2017/00349* (2013.01); *A61B 2017/00367* (2013.01); *A61B 2017/00827* (2013.01);
(Continued)

(58) Field of Classification Search
CPC ................. A61B 17/0401; A61B 2017/00827; A61B 2017/0403; A61B 2017/0409; A61B 2017/0414; A61B 2017/0419

USPC .......................................... 606/139, 142, 144
See application file for complete search history.

(56) References Cited

U.S. PATENT DOCUMENTS

| 2,753,870 A | 7/1956 | Muffly |
| 3,875,928 A | 4/1975 | Angelchik |

(Continued)

FOREIGN PATENT DOCUMENTS

| EP | 252607 A2 | 9/1992 |
| WO | 9922649 A2 | 5/1999 |

(Continued)

OTHER PUBLICATIONS

The gastroesophageal flap valve: in vitro and in vivo observations; Lucius D. Hill et al.; Gastrointestinal Endoscopy; vol. 44, No. 5, 1996; pp. 541-547; abstract.

(Continued)

*Primary Examiner* — Katherine Rodjom
*Assistant Examiner* — Jonathan Hollm
(74) *Attorney, Agent, or Firm* — Fulwider Patton LLP

(57) ABSTRACT

A patient's stomach may be secured to the patient's diaphragm. A method to accomplish this includes visualizing a wall of a patient's stomach adjacent the patient's diaphragm from within the patient's stomach, inserting a fastener deployment apparatus down the patient's esophagus and into the mammalian's stomach, and fastening the patient's stomach to the patient's diaphragm with the fastener deployment apparatus and from within the stomach. The procedure may be employed to advantage to treat a hiatal hernia, for example, either alone or in conjunction with the restoration of the patient's gastroesophageal flap valve.

2 Claims, 8 Drawing Sheets

(51) Int. Cl.
*A61B 17/11* (2006.01)
*A61B 17/29* (2006.01)
*A61B 17/00* (2006.01)
*A61B 17/08* (2006.01)

(52) U.S. Cl.
CPC  *A61B 2017/0409* (2013.01); *A61B 2017/0419* (2013.01); *A61B 2017/0445* (2013.01); *A61B 2017/081* (2013.01)

(56) References Cited

U.S. PATENT DOCUMENTS

| | | |
|---|---|---|
| 4,006,747 A | 2/1977 | Kronenthal |
| 4,271,828 A | 6/1981 | Angelchik |
| 4,576,772 A | 3/1986 | Carpenter et al. |
| 4,595,007 A | 6/1986 | Mericle |
| 4,669,473 A | 6/1987 | Richards et al. |
| 4,696,300 A | 9/1987 | Anderson |
| 4,846,836 A | 7/1989 | Reich |
| 4,895,148 A | 1/1990 | Bays et al. |
| 4,921,479 A | 5/1990 | Grayzel |
| 5,006,106 A | 4/1991 | Angelchik et al. |
| 5,041,129 A * | 8/1991 | Hayhurst et al. ............ 606/232 |
| 5,080,543 A | 1/1992 | Murphy |
| 5,088,979 A | 2/1992 | Filipi et al. |
| 5,254,126 A | 10/1993 | Filipi et al. |
| 5,314,473 A | 5/1994 | Godin |
| 5,403,326 A | 4/1995 | Harrison et al. |
| 5,411,508 A | 5/1995 | Bessler et al. |
| 5,411,520 A | 5/1995 | Nash et al. |
| 5,549,621 A | 8/1996 | Bessler et al. |
| 5,571,074 A | 11/1996 | Buckman et al. |
| 5,571,116 A | 11/1996 | Bolanos et al. |
| 5,626,614 A * | 5/1997 | Hart ............................ 606/232 |
| 5,676,674 A | 10/1997 | Bolanos et al. |
| 5,713,903 A | 2/1998 | Sander et al. |
| 5,759,151 A | 6/1998 | Sturges |
| 5,810,882 A | 9/1998 | Bolduc et al. |
| 5,814,054 A | 9/1998 | Kortenbach et al. |
| 5,861,036 A | 1/1999 | Godin |
| 5,879,372 A | 3/1999 | Bartlett et al. |
| 5,887,594 A | 3/1999 | LoCicero |
| 5,897,562 A | 4/1999 | Bolanos et al. |
| 5,938,668 A | 8/1999 | Scirica et al. |
| 6,086,600 A | 7/2000 | Kortenbach |
| 6,091,995 A * | 7/2000 | Ingle et al. ................... 607/138 |
| 6,098,629 A | 8/2000 | Johnson et al. |
| 6,113,609 A | 9/2000 | Adams |
| 6,113,611 A | 9/2000 | Allen et al. |
| 6,142,957 A | 11/2000 | Diamond et al. |
| 6,254,642 B1 | 7/2001 | Taylor |
| 6,264,700 B1 | 7/2001 | Kilcoyne et al. |
| 6,302,311 B1 | 10/2001 | Adams et al. |
| 6,302,917 B1 | 10/2001 | Dua et al. |
| 6,312,437 B1 | 11/2001 | Kortenbach |
| 6,315,789 B1 | 11/2001 | Cragg |
| 6,419,669 B1 | 7/2002 | Frazier et al. |
| 6,428,548 B1 | 8/2002 | Durgin et al. |
| 6,447,524 B1 | 9/2002 | Knodel et al. |
| 6,506,196 B1 * | 1/2003 | Laufer .......................... 606/142 |
| 6,547,776 B1 * | 4/2003 | Gaiser et al. ................. 604/506 |
| 6,663,639 B1 * | 12/2003 | Laufer et al. ................ 606/139 |
| 6,736,828 B1 * | 5/2004 | Adams et al. ................ 606/213 |
| 6,743,239 B1 | 6/2004 | Kuehn et al. |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,835,200 B2 | 12/2004 | Laufer et al. |
| 6,916,332 B2 | 7/2005 | Adams |
| 6,921,361 B2 | 7/2005 | Suzuki et al. |
| 7,022,118 B2 | 4/2006 | Ariura et al. |
| 7,037,344 B2 | 5/2006 | Kagan et al. |
| 7,074,229 B2 | 7/2006 | Adams et al. |
| 7,083,630 B2 | 8/2006 | DeVries et al. |
| 7,220,266 B2 | 5/2007 | Gambale |
| 7,347,863 B2 | 3/2008 | Rothe et al. |
| 7,452,364 B2 * | 11/2008 | Schreiber et al. ............ 606/153 |
| 7,618,426 B2 | 11/2009 | Ewers et al. |
| 7,632,287 B2 | 12/2009 | Baker et al. |
| 7,678,123 B2 | 3/2010 | Chanduszko |
| 7,713,277 B2 | 5/2010 | Laufer et al. |
| 7,776,057 B2 | 8/2010 | Laufer et al. |
| 7,850,704 B2 | 12/2010 | Burnett et al. |
| 7,857,184 B2 | 12/2010 | Viola |
| 7,857,823 B2 | 12/2010 | Laufer et al. |
| 7,866,526 B2 | 1/2011 | Green et al. |
| 7,942,887 B2 | 5/2011 | Kraemer et al. |
| 7,951,157 B2 | 5/2011 | Gambale |
| 7,954,687 B2 | 6/2011 | Zemlok et al. |
| 7,955,340 B2 | 6/2011 | Michlitsch et al. |
| 8,057,494 B2 | 11/2011 | Laufer et al. |
| 8,252,009 B2 | 8/2012 | Weller et al. |
| 8,277,468 B2 | 10/2012 | Laufer et al. |
| 8,308,765 B2 | 11/2012 | Saadat et al. |
| 8,343,175 B2 | 1/2013 | Ewers et al. |
| 8,574,243 B2 | 11/2013 | Saadat et al. |
| 2002/0022853 A1 | 2/2002 | Swanson et al. |
| 2002/0035370 A1 | 3/2002 | Kortenbach |
| 2002/0040226 A1 | 4/2002 | Laufer et al. |
| 2002/0055772 A1 | 5/2002 | McGuckin, Jr. et al. |
| 2002/0072761 A1 | 6/2002 | Abrams et al. |
| 2002/0078967 A1 | 6/2002 | Sixto, Jr. et al. |
| 2002/0082621 A1 | 6/2002 | Schurr et al. |
| 2002/0143349 A1 | 10/2002 | Gifford, III et al. |
| 2002/0183765 A1 | 12/2002 | Adams |
| 2002/0198541 A1 | 12/2002 | Smith et al. |
| 2003/0023230 A1 | 1/2003 | Lewis et al. |
| 2003/0055442 A1 | 3/2003 | Laufer et al. |
| 2003/0065359 A1 | 4/2003 | Weller et al. |
| 2003/0093117 A1 | 5/2003 | Saadat |
| 2003/0120289 A1 | 6/2003 | McGuckin, Jr. et al. |
| 2003/0120292 A1 | 6/2003 | Park et al. |
| 2003/0171760 A1 | 9/2003 | Gambale |
| 2003/0187465 A1 | 10/2003 | Bailly et al. |
| 2003/0191497 A1 | 10/2003 | Cope |
| 2003/0216613 A1 | 11/2003 | Suzuki et al. |
| 2003/0216754 A1 * | 11/2003 | Kraemer et al. ............ 606/142 |
| 2003/0220657 A1 | 11/2003 | Adams |
| 2003/0220660 A1 * | 11/2003 | Kortenbach et al. ......... 606/151 |
| 2004/0044304 A1 | 3/2004 | Hill et al. |
| 2004/0044364 A1 * | 3/2004 | DeVries et al. ............. 606/213 |
| 2004/0087976 A1 | 5/2004 | DeVries et al. |
| 2004/0093024 A1 | 5/2004 | Lousararian et al. |
| 2004/0116949 A1 * | 6/2004 | Ewers et al. ................ 606/167 |
| 2004/0133236 A1 | 7/2004 | Chanduszko |
| 2004/0138529 A1 | 7/2004 | Wiltshire et al. |
| 2004/0147958 A1 | 7/2004 | Lam et al. |
| 2004/0148034 A1 | 7/2004 | Kagan et al. |
| 2004/0153102 A1 | 8/2004 | Therin et al. |
| 2004/0153103 A1 | 8/2004 | Schwartz et al. |
| 2004/0158264 A1 * | 8/2004 | Adams et al. ............... 606/139 |
| 2004/0162465 A1 * | 8/2004 | Carrillo ........................ 600/104 |
| 2004/0162568 A1 | 8/2004 | Saadat et al. |
| 2004/0215216 A1 | 10/2004 | Gannoe et al. |
| 2004/0236357 A1 | 11/2004 | Kraemer et al. |
| 2004/0243223 A1 | 12/2004 | Kraemer et al. |
| 2005/0004575 A1 | 1/2005 | Sgro et al. |
| 2005/0017781 A1 | 1/2005 | Honda |
| 2005/0043759 A1 | 2/2005 | Chanduszko |
| 2005/0075653 A1 | 4/2005 | Saadat et al. |
| 2005/0085829 A1 | 4/2005 | Kraemer et al. |
| 2005/0154405 A1 | 7/2005 | Kraemer et al. |
| 2005/0177176 A1 | 8/2005 | Gerbi et al. |
| 2005/0187565 A1 * | 8/2005 | Baker et al. ................ 606/151 |
| 2005/0203547 A1 | 9/2005 | Weller et al. |
| 2005/0216040 A1 | 9/2005 | Gertner et al. |
| 2005/0228413 A1 | 10/2005 | Binmoeller et al. |
| 2005/0247320 A1 | 11/2005 | Stack et al. |
| 2005/0251176 A1 | 11/2005 | Swanstrom et al. |
| 2006/0009789 A1 | 1/2006 | Gambale |
| 2006/0190018 A1 | 8/2006 | Baker et al. |
| 2006/0253130 A1 * | 11/2006 | Wolniewicz, III . A61B 17/0401 606/142 |
| 2006/0253131 A1 * | 11/2006 | Wolniewicz, III ...... A61B 17/10 |

(56) References Cited

U.S. PATENT DOCUMENTS

| | | | |
|---|---|---|---|
| | | | 606/142 |
| 2006/0253142 A1 | 11/2006 | Bjerken | |
| 2007/0005080 A1* | 1/2007 | Wolniewicz et al. | ......... 606/142 |
| 2007/0021756 A1 | 1/2007 | Kortenbach | |
| 2007/0021760 A1 | 1/2007 | Kelleher | |
| 2007/0112363 A1 | 5/2007 | Adams | |
| 2007/0129738 A1 | 6/2007 | Kraemer et al. | |
| 2007/0191870 A1 | 8/2007 | Baker et al. | |
| 2007/0191871 A1 | 8/2007 | Baker et al. | |
| 2007/0219566 A1 | 9/2007 | Gambale | |
| 2007/0276409 A1 | 11/2007 | Ortiz et al. | |
| 2008/0015618 A1 | 1/2008 | Sonnenschein et al. | |
| 2008/0287966 A1 | 11/2008 | Kraemer et al. | |
| 2008/0294179 A1 | 11/2008 | Balbierz et al. | |
| 2009/0177214 A1 | 7/2009 | Adams | |
| 2009/0198254 A1 | 8/2009 | Laufer et al. | |
| 2009/0236388 A1 | 9/2009 | Cole et al. | |
| 2010/0241139 A1 | 9/2010 | Harshman | |
| 2011/0196391 A1 | 8/2011 | Forsell | |
| 2011/0213390 A1 | 9/2011 | Kraemer et al. | |

FOREIGN PATENT DOCUMENTS

| | | | |
|---|---|---|---|
| WO | 9960931 | A1 | 12/1999 |
| WO | 0053102 | A1 | 9/2000 |
| WO | 0078227 | A1 | 12/2000 |
| WO | 0132084 | A1 | 5/2001 |
| WO | 0135834 | A1 | 5/2001 |
| WO | 0164964 | A1 | 9/2001 |
| WO | 0167964 | A2 | 9/2001 |
| WO | 0185034 | A1 | 11/2001 |
| WO | 0189391 | A1 | 11/2001 |
| WO | 0224058 | A2 | 3/2002 |
| WO | 0224080 | A2 | 3/2002 |
| WO | 0228289 | A1 | 4/2002 |
| WO | 02082621 | A1 | 10/2002 |
| WO | 02096327 | A2 | 12/2002 |
| WO | 03061480 | A1 | 7/2003 |
| WO | 03099140 | A1 | 12/2003 |
| WO | 2004019787 | A2 | 3/2004 |
| WO | 2004019788 | A2 | 3/2004 |
| WO | 2004049982 | A2 | 6/2004 |
| WO | 2004069055 | A2 | 8/2004 |
| WO | 2005065412 | A2 | 7/2005 |
| WO | 2005081817 | A2 | 9/2005 |
| WO | 2006023764 | A2 | 3/2006 |
| WO | 2006034484 | A2 | 3/2006 |
| WO | 2006081368 | A2 | 8/2006 |
| WO | 2007002817 | A2 | 1/2007 |
| WO | 2007064713 | A2 | 6/2007 |
| WO | 2010087756 | A1 | 8/2010 |

OTHER PUBLICATIONS

Reappraisal of the flap valve mechanism in the gastroesophageal junction: A study of a new valvuloplasty procedure in cadavers; KjellB.A. Thor et al.; Acta Chir Scand 153:25-28, 1987; abstract.
The Plicator Procedure; 1 page; abstract.
Chuttani, MD. et al., "A novel endoscopic full-thickness plicator for treatment of GERD: an animal model study". Gastrointestinal Endoscopy, vol. 56, No. 1, 2002, pp. 116-122; abstract.
Jobe, et al., "Endoscopic Appraisal of the Gastroesophageal Valve After Antireflux Surgery", American Journal of Gastroenterology, ISSN 0002-9270; abstract.
International Search Report for PCT/US2012/054328.

* cited by examiner

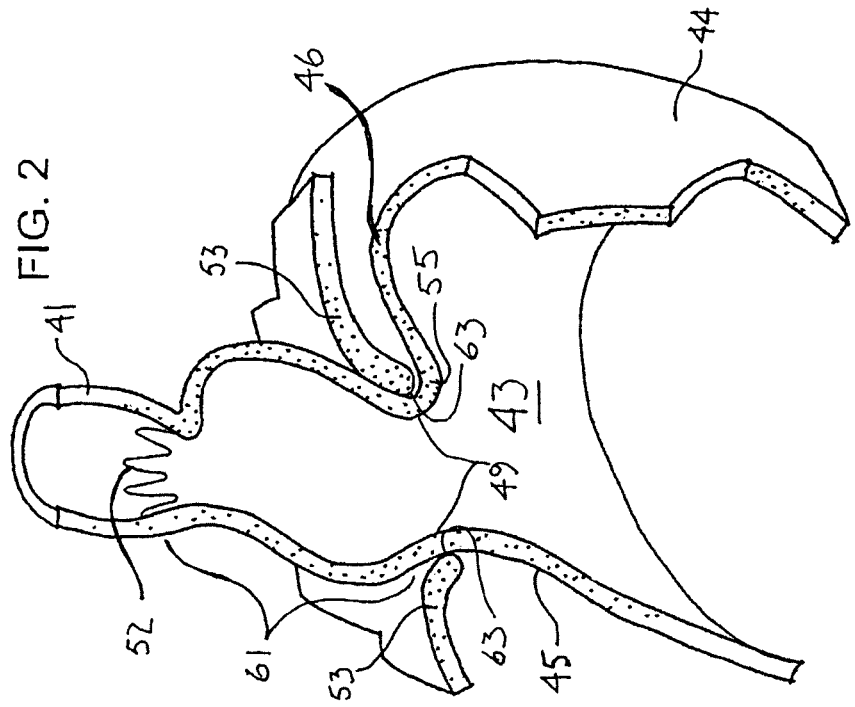
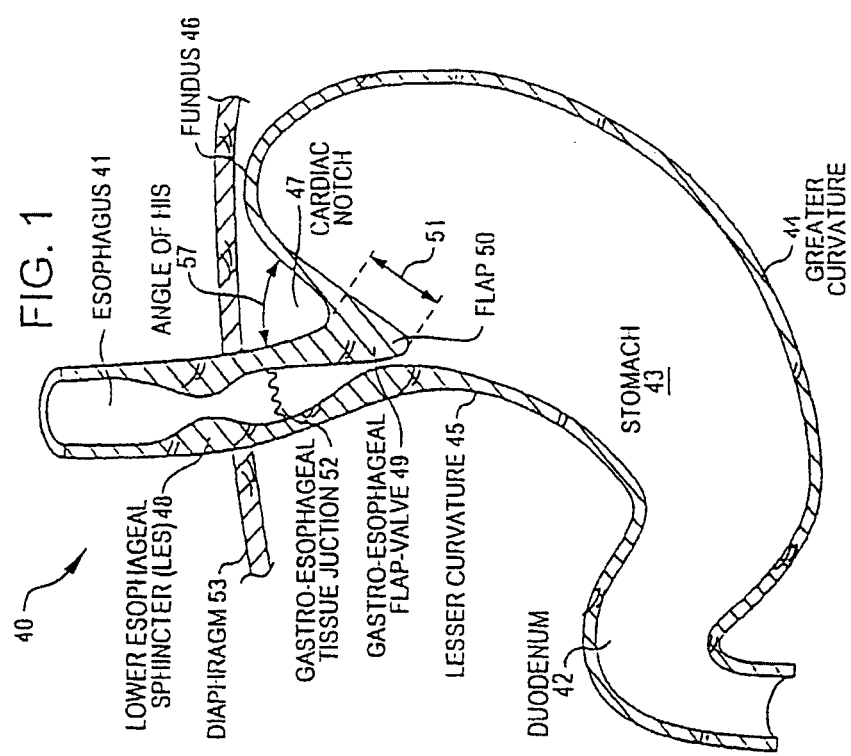

APPARATUS AND METHOD FOR SECURING THE STOMACH TO THE DIAPHRAGM FOR USE, FOR EXAMPLE, IN TREATING HIATAL HERNIAS AND GASTROESOPHAGEAL REFLUX DISEASE

This application is a divisional application of U.S. application Ser. No. 11/203,680, filed Aug. 12, 2005 now abandoned. The entire disclosure of which is hereby incorporated for all purposes.

FIELD OF THE INVENTION

The present invention generally relates to securing the stomach to the diaphragm to treat (or as integral part of treating . . . ), for example, hiatal hernias and gastroesophageal reflux disease. The present invention more particularly relates to fixing the stomach to the diaphragm transorally without the need for invasive surgical incisions.

BACKGROUND

A hiatal hernia is an anatomical abnormality in which part of the stomach protrudes through the diaphragm and up into the chest. Hiatal hernias are present in approximately 15% of the population and its occurrence increases with age. Recent studies estimate that it is present in 60-65% of those over 60 years of age.

Normally, the esophagus or food tube passes down through the chest, crosses the diaphragm, and enters the abdomen through a hole in the diaphragm called the esophageal hiatus. This "hole" is a muscular tube or channel of about two to three vertebrae in length. Just below the diaphragm, the esophagus joins the stomach at the gastroesophageal junction. In individuals with hiatal hernias, the opening of the esophageal hiatus (hiatal opening) is larger than normal, and a portion of the upper stomach slips up or passes (herniates) through the hiatus and into the chest. Although hiatal hernias are occasionally seen in infants where they probably have been present from birth, most hiatal hernias in adults are believed to have developed over many years.

It is thought that hiatal hernias develop as a part of permanent positive pressure in the abdomen and negative pressure in the chest with thousands of daily unsynchronized movements of the esophagus and diaphragm. Over time, the phrenoesophageal bundles or membrane elongate, allowing the gastroesophageal junction (GEJ) to slip into the chest. Widening is currently thought of as being the result of mechanical dilatation and recurrent inflammation in the herniated stomach (often referred to as the acid chamber), which leads to periesophagitis and retraction of the diaphragmatic muscle over time. As a result of the large opening, part of the stomach "slips" into the chest. Another potentially contributing factor is an abnormally loose attachment of the esophagus to the diaphragm, which allows the esophagus and stomach to slip upwards.

Hiatal hernias are categorized as being either sliding or para-esophageal. Sliding hiatal hernias are those in which the junction of the esophagus and stomach, referred to as the gastro-esophageal junction, and part of the stomach protrude into the chest. The junction may reside permanently in the chest, but often it juts into the chest only during a swallow or if the patient is in a recumbent position. This occurs because with each swallow the muscle of the esophagus contracts causing the esophagus to shorten and to pull up the stomach through the widened diaphragm. When the swallow is finished, the esophagus relaxes and the herniated part of the stomach falls back into the abdomen. Para-esophageal hernias are hernias in which the gastro-esophageal junction stays where it belongs (attached at the level of the diaphragm), but part of the stomach passes or bulges into the chest beside the esophagus. The para-esophageal hernias themselves may remain in the chest at all times and are not affected by swallows.

A para-esophageal hiatal hernia that is large, particularly if it compresses the adjacent esophagus, may impede the passage of food into the stomach and cause food to stick in the esophagus after it is swallowed. Ulcers also may form in the herniated stomach due to the trauma caused by food that is stuck or acid from the stomach. Fortunately, large para-esophageal hernias are uncommon.

The vast majority of hiatal hernias are of the sliding type. The larger the hernia, the more likely it is to cause symptoms. When hiatal hernias produce symptoms, they may also be associated with gastro-esophageal reflux disease (GERD), to be described herein after, or its complications. GERD can occur because the formation of the hernia often interferes with the natural barrier, which prevents acid from refluxing from the stomach into the esophagus. Patients with GERD are much more likely to have a hiatal hernia than individuals not afflicted by GERD. Thus, it is clear that hiatal hernias contribute to GERD.

Normally, there are several mechanisms to prevent acid from flowing backwards (refluxing) up into the esophagus. One mechanism involves a band of esophageal muscle where the esophagus joins the stomach called the lower esophageal sphincter that remains contracted most of the time to prevent acid from refluxing or regurgitating. The sphincter only relaxes when food is swallowed so that the food can pass from the esophagus and into the stomach. The area of the sphincter normally is attached firmly to the diaphragm in the hiatus through the phrenoesophageal membrane, and the muscle of the diaphragm, also called the crura of the diaphragm, wraps around the gastroesophageal junction and the sphincter, much like a scarf. The muscle that wraps around the diaphragm augments the pressure of the contracted sphincter and the gastroesophageal junction to further prevent reflux of acid.

Another mechanism that prevents reflux is the valve-like tissue at the junction of the esophagus and stomach just below the sphincter. The esophagus normally enters the stomach tangentially so that there is a sharp angle between the esophagus and stomach. The piece of tissue in this angle, composed of esophageal and stomach wall, forms a valve that can close off the opening to the esophagus at all times and even more, when pressure increases in the stomach, for example, during eating, when the stomach is filled. It can however open to allow gastric air or contents to pass into the esophagus in a healthy subject, e.g. during belching or vomiting.

When a hiatal hernia is present, two changes occur. First, the sphincter slides up into the chest while the diaphragm remains stationery. As a result, the pressure normally generated by the diaphragm overlying the sphincter and the pressure generated by the sphincter no longer overlap, and as a result, the total pressure at the gastro-esophageal junction decreases. Second, when the gastro-esophageal junction and stomach are pulled up into the chest with each swallow, the sharp angle where the esophagus joins the stomach becomes less sharp and the valve-like effect is lost. Both changes promote reflux of acid. With the diaphragm pinching the herniated stomach and the LES closing the esophagus, an "acid chamber" may result, leading to severe esophagitis with periesophagitis and potentially ulceration and bleeding. Due to the periesophagitis, the crura also retract, leading to a widening of the diaphragmatic opening over time and worsening of the hiatus hernia.

Hiatal hernias are diagnosed incidentally when an upper gastrointestinal x-ray or endoscopy is done during testing to determine the cause of upper gastrointestinal symptoms such as upper abdominal pain. On both the x-ray and endoscopy, the hiatal hernia appears as a separate "sac" lying between what is clearly the esophagus and what is clearly the stomach. This sac is delineated by the lower esophageal sphincter above and the diaphragm below.

Treatment of large para-esophageal hernias causing symptoms requires surgery. During surgery, the stomach is accessed invasively through incisions made in the abdomen or in the chest. The stomach is pulled down into the abdomen, the esophageal hiatus is made smaller, and the esophagus is attached to the diaphragm with sutures. Although the procedure restores the normal anatomy, it is invasive, requiring weeks or even months of recovery before all normal activity may be resumed.

As will be seen subsequently, the present invention provides an alternative procedure for treating hiatal hernias. Instead of being surgically invasive, the new procedure, according to the various embodiments described herein after, may be performed transorally without the need for invasive incisions. As a result, patients are able to recover much more quickly and return to normal activity within a few days.

Gastroesophageal reflux disease (GERD) is a chronic condition caused by the failure of the anti-reflux barrier located at the gastroesophageal junction to keep the contents of the stomach from splashing into the esophagus. The splashing is known as gastroesophageal reflux. The stomach acid is designed to digest meat and other foods, and will digest esophageal tissue when persistently splashed into the esophagus.

A principal reason for regurgitation associated with GERD is the mechanical failure of a deteriorated gastroesophageal valve to close and seal against high pressure in the stomach. Due to reasons including lifestyle, a Grade I normal gastroesophageal valve may deteriorate into a malfunctioning Grade III or absent valve Grade IV. With a deteriorated gastroesophageal valve, the stomach contents are more likely to be regurgitated into the esophagus, the mouth, and even the lungs. The regurgitation is referred to as "heartburn" because the most common symptom is a burning discomfort in the chest under the breastbone. Burning discomfort in the chest and regurgitation (burping up) of sour-tasting gastric juice into the mouth are classic symptoms of gastroesophageal reflux disease (GERD). When stomach acid is regurgitated into the esophagus, it is usually cleared quickly by esophageal contractions. Heartburn (backwashing of stomach acid and bile onto the esophagus) results when stomach acid is frequently regurgitated into the esophagus and the esophageal wall is inflamed.

Complications develop for some people who have GERD. Esophagitis (inflammation of the esophagus) with erosions and ulcerations (breaks in the lining of the esophagus) can occur from repeated and prolonged acid exposure. If these breaks are deep, bleeding or scarring of the esophagus with formation of a stricture (narrowing of the esophagus) can occur. If the esophagus narrows significantly, then food sticks in the esophagus and the symptom is known as dysphagia. GERD has been shown to be one of the most important risk factors for the development of esophageal adenocarcinoma. In a subset of people who have severe GERD, if acid exposure continues, the injured squamous lining is replaced by a pre-cancerous lining (called Barrett's Esophagus) in which a cancerous esophageal adenocarcinoma can develop.

Other complications of GERD may not appear to be related to esophageal disease at all. Some people with GERD may develop recurrent pneumonia (lung infection), asthma (wheezing), or a chronic cough from acid backing up into the esophagus and all the way up through the upper esophageal sphincter into the lungs. In many instances, this occurs at night, while the person is in a supine position and sleeping. Occasionally, a person with severe GERD will be awakened from sleep with a choking sensation. Hoarseness can also occur due to acid reaching the vocal cords, causing a chronic inflammation or injury.

GERD never improves without intervention. Life style changes combined with both medical and surgical treatments exist for GERD. Medical therapies include antacids and proton pump inhibitors. However, the medical therapies only mask the reflux. Patients still get reflux and perhaps emphysema because of particles refluxed into the lungs. Barrett's esophagus results in about 10% of the GERD cases. The esophageal epithelium changes into tissue that tends to become cancerous from repeated acid washing despite the medication.

Several open laparotomy and laparoscopic surgical procedures are available for treating GERD. One surgical approach is the Nissen fundoplication. The Nissen approach typically involves a 360-degree wrap of the fundus around the gastroesophageal junction. The procedure has a high incidence of postoperative complications. The Nissen approach creates a 360-degree moveable valve without a fixed portion. Hence, Nissen does not restore the normal movable valve. The patient cannot burp because the fundus was used to make the repair, and may frequently experience dysphagia. Another surgical approach to treating GERD is the Belsey Mark IV (Belsey) fundoplication. The Belsey procedure involves creating a valve by suturing a portion of the stomach to an anterior surface of the esophagus. It reduces some of the postoperative complications encountered with the Nissen fundoplication, but still does not restore the normal movable valve. None of these procedures fully restores the normal anatomy or produces a normally functioning gastroesophageal junction. Another surgical approach is the Hill repair. In the Hill repair, the gastroesophageal junction is anchored to the posterior abdominal areas, and a 180-270 degree valve is created by a system of sutures. The Hill procedure restores the moveable portion of the valve, the cardiac notch and the Angle of His. However, all of these surgical procedures are very invasive, regardless of whether done as a laparoscopic or an open procedure.

New, less surgically invasive approaches to treating GERD involve transoral endoscopic procedures. One procedure contemplates a machine device with robotic arms that is inserted transorally into the stomach. While observing through an endoscope, an endoscopist guides the machine within the stomach to engage a portion of the fundus with a corkscrew-like device at the hinge point. The arm then pulls on the engaged portion to create a fold of tissue or radial plication at the gastroesophageal junction. The angle of His or the valve remain unaltered. Another arm of the machine pinches the excess tissue together and fastens the excess tissue with one pre-tied implant. This procedure does not restore normal anatomy. The fold created does not have anything in common with a valve. In fact, the direction of the radial fold prevents the fold or plication from acting as a flap of a valve.

Another transoral procedure contemplates making a fold of fundus tissue near the deteriorated gastroesophageal flap to recreate the lower esophageal sphincter (LES). The procedure requires placing multiple U-shaped tissue clips around the folded fundus to hold it in shape and in place.

This and the previously discussed procedure are both highly dependent on the skill, experience, aggressiveness, and courage of the endoscopist. In addition, these and other procedures may involve esophageal tissue in the repair. Esophageal tissue is fragile and weak, in part due to the fact, that the esophagus is not covered by serosa, a layer of very sturdy, yet very thin tissue, covering and stabilizing all intraabdominal organs, similar like a fascia covering and stabilizing muscle. Involvement of esophageal tissue in the repair of a gastroesophageal valve poses unnecessary risks to the patient, such as an increased risk of fistulas between the esophagus and the stomach.

A new and improved apparatus and method for restoration of a gastroesophageal flap valve is fully disclosed in U.S. Pat. No. 6,790,214, issued Sep. 14, 2004, is assigned to the assignee of this invention, and is incorporated herein by reference. That apparatus and method provides a transoral endoscopic gastroesophageal flap valve restoration. A longitudinal member arranged for transoral placement into a stomach carries a tissue shaper that non-invasively grips and shapes stomach tissue. A tissue fixation device is then deployed to maintain the shaped stomach tissue in a shape approximating a gastroesophageal flap.

Since transoral GEFV restoration is a certain reality, it would be most desirable to be able to treat potentially related hiatal hernias in a similar manner to avoid invasive surgery altogether. The present invention addresses this and other issues.

SUMMARY

The invention provides a method comprising visualizing a wall of a patient's stomach adjacent the patient's diaphragm from within the patient's stomach, inserting a fastener deployment apparatus down the patient's esophagus and into the patient's stomach, and fastening the patient's stomach to the patient's diaphragm with the fastener deployment apparatus and from within the stomach. The fastening step may include fastening the patient's stomach to a crus of the patient's diaphragm, such as the right crus or to the muscular or tendenous portion of the diaphragm. The fastening step may in addition or alternatively include fastening the fundus of the patient's stomach to the patient's diaphragm.

The invention further provides an assembly comprising an elongated member including a proximal end and a distal end, and a fastener deployer carried at the distal end of the elongated member. The elongated member and fastener deployer are arranged to feed the fastener deployer down a throat and esophagus into a stomach. The fastener deployer is further arranged to fasten the stomach to an adjacent diaphragm. The assembly further comprises a visualization device that enables visualization of the stomach being fastened to the adjacent diaphragm.

The fastener deployer may be arranged to fasten the stomach to a crus of the diaphragm, such as the right crus. The fastener deployer may alternatively or additionally be arranged to fasten the fundus of the stomach to the diaphragm. The fastener deployer may comprise an elongated arm that positions the fastener deployer spaced away from the esophageal opening to the stomach and in contact with the fundus.

The visualization device may comprise an endoscope.

The elongated member may include a guide that guides the visualization device into the stomach.

The fastener deployer may include at least one fastener to be deployed. The fastener may comprise a first member, a second member, the first and second members having first and second ends, and a connecting member fixed to each of the first and second members intermediate the first and second ends and extending between the first and second members. The first and second members are separated by the connecting member. One of the first and second members has a through channel along the axis arranged to be slidingly received on a tissue piercing deployment wire.

The fastener may further comprise a slit extending between the first and second ends and communicating with the through channel.

The fastener deployer may further comprise a deployment wire arranged to be slidingly received by the through channel of the one of the first and second members, to pierce into the tissue to be fastened, and to guide the fastener into the tissue. The fastener deployer may further comprise a pusher that pushes the one of first and second members into the tissue while on the deployment wire and a guide tube extending over the deployment wire and the fastener that guides the deployment wire and fastener to the tissue. The fastener deployer may still further comprise an elongated arm that supports and positions the guide tube spaced away from the esophageal opening to the stomach and in proximity with fundus of the stomach.

The invention still further provides a method of treating a stomach disorder. The method comprises providing a transoral gastroesophageal valve restoration device, feeding the device down the esophagus into the stomach, forming a gastroesophageal valve with the device from within the stomach, fastening stomach tissue to maintain the gastroesophageal valve, and securing the stomach to the diaphragm from within the stomach.

The step of securing the stomach to the diaphragm may include fastening the stomach to a crus of the diaphragm, such as the right crus. The step of securing the stomach to the diaphragm may alternatively or additionally include fastening fundus of the stomach to the diaphragm.

The method may further comprise gripping the esophagus and displacing the esophagus until the stomach is completing within the diaphragm before securing the stomach to the diaphragm. The steps of gripping the esophagus and displacing the esophagus until the stomach is completing within the diaphragm may be performed before the step of forming a gastroesophageal valve with the device from within the stomach.

The invention still further provides a method of treating a hiatal hernia of a patient associated with the patient's esophagus, stomach, and diaphragm. The method comprises the steps of gripping the esophagus, displacing the esophagus towards the diaphragm until the stomach is completely positioned below the diaphragm, and securing the stomach to the diaphragm. The gripping, displacing, and securing steps are performed transorally.

The step of securing the stomach to the diaphragm may include fastening the stomach to the right crus of the diaphragm. The step of securing the stomach to the diaphragm may alternatively or additionally include fastening fundus of the stomach to the diaphragm.

The gripping step may include gripping sidewalls of the esophagus. The sidewalls of the stomach may be gripped with a vacuum.

The invention further provides a fastener deployment apparatus that deploys a fastener in body tissue. The apparatus comprises a window permitting visualization of internal body anatomy when placed in a body, a location marker viewable in the window, and a fastener deployer having a predetermined orientation relative to the location marker that ejects a fastener for deployment at a predetermined location relative to the location marker.

The invention further provides a method of treating a hiatal hernia and restoring a gastroesophageal valve of a patient. The method comprises the steps of gripping the esophagus, displacing the esophagus aborally to reduce the hiatal hernia, and manipulating tissue of the stomach while maintaining a grip on the esophagus to restore the gastroesophageal valve. The gripping, displacing, and manipulating steps are performed transorally.

The method may further comprise the step of securing the stomach to the diaphragm. The manipulating step may include forming a gastroesophageal valve flap and the method may further comprise deploying at lease one fastener through the gastroesophageal valve flap to maintain the valve and the reduced hiatal hernia.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify like elements, and wherein:

FIG. 1 is a front cross-sectional view of the esophageal-gastro-intestinal tract from a lower portion of the esophagus to the duodenum;

FIG. 2 is a partial perspective view with portions cut away of a stomach, esophagus, and diaphragm illustrating a hiatal hernia which may be treated according to an embodiment of the invention;

DETAILED DESCRIPTION

Figure 3:
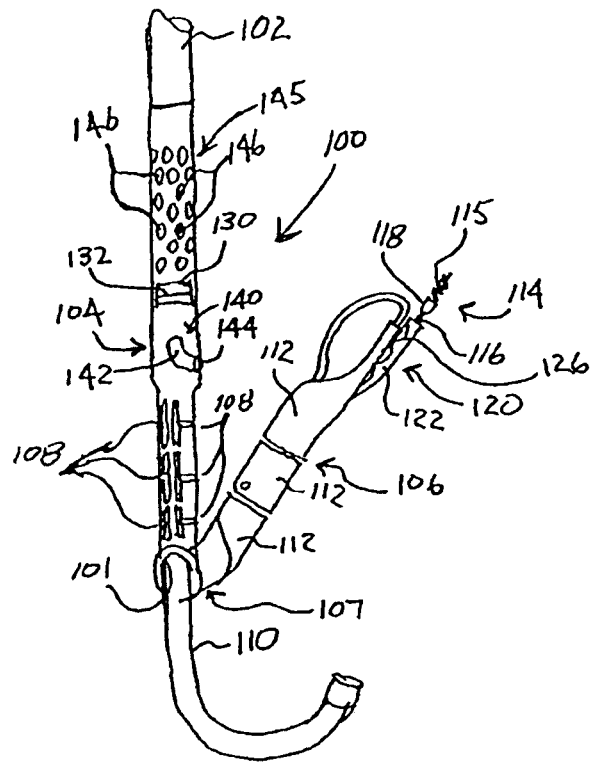
FIG. 3 is a side view of an apparatus for restoring a GEFV and securing the stomach to the diaphragm according to an embodiment of the invention.

FIG. 1 is a front cross-sectional view of the esophageal-gastro-intestinal tract 40 from a lower portion of the esophagus 41 to the duodenum 42. The stomach 43 is characterized by the greater curvature 44 on the anatomical left side and the lesser curvature 45 on the anatomical right side. The tissue of the outer surfaces of those curvatures is referred to in the art as serosa tissue. As will be seen subsequently, the nature of the serosa tissue is used to advantage for its ability to bond to like serosa tissue.

The fundus 46 of the greater curvature 44 forms the superior portion of the stomach 43, and traps gas and air bubbles for burping. The esophageal tract 41 enters the stomach 43 at an esophageal orifice below the superior portion of the fundus 46, forming a cardiac notch 47 and an acute angle with respect to the fundus 46 known as the Angle of His 57. The lower esophageal sphincter (LES) 48 is a discriminating sphincter able to distinguish between burping gas, liquids, and solids, and works in conjunction with the fundus 46 to burp. The gastroesophageal flap valve (GEFV) 49 includes a moveable portion and an opposing more stationary portion.

The moveable portion of the GEFV 49 is an approximately 180 degree, semicircular, gastroesophageal flap 50 (alternatively referred to as a "normal moveable flap" or "moveable flap") formed of tissue at the intersection between the esophagus 41 and the stomach 43. The opposing more stationary portion of the GEFV 49 comprises a portion of the lesser curvature 45 of the stomach 43 adjacent to its junction with the esophagus 41. The gastroesophageal flap 50 of the GEFV 49 principally comprises tissue adjacent to the fundus 46 portion of the stomach 43. It is about 4 to 5 cm long (51) at it longest portion, and its length may taper at its anterior and posterior ends.

The gastroesophageal flap 50 is partially held against the lesser curvature 45 portion of the stomach 43 by the pressure differential between the stomach 43 and the thorax, and partially by the resiliency and the anatomical structure of the GEFV 49, thus providing the valving function. The GEFV 49 is similar to a flutter valve, with the gastroesophageal flap 50 being flexible and closeable against the other more stationary side.

The esophageal tract is controlled by an upper esophageal sphincter (UES) in the neck near the mouth for swallowing, and by the LES 48 and the GEFV 49 at the stomach. The normal anti-reflux barrier is primarily formed by the LES 48 and the GEFV 49 acting in concert to allow food and liquid to enter the stomach, and to considerably resist reflux of stomach contents into the esophagus 41 past the gastroesophageal tissue junction 52. Tissue aboral of the gastroesophageal tissue junction 52 is generally considered part of the stomach because the tissue protected from stomach acid by its own protective mechanisms. Tissue oral of the gastroesophageal junction 52 is generally considered part of the esophagus and it is not protected from injury by prolonged exposure to stomach acid. At the gastroesophageal junction 52, the juncture of the stomach and esophageal tissues form a zigzag line, which is sometimes referred to as the "Z-line." For the purposes of these specifications, including the claims, "stomach" means the tissue aboral of the gastroesophageal junction 52.

FIG. 2 is a perspective view, with portions cut away, of stomach 43, esophagus 41, diaphragm 53, and hiatal hernia 61 which may be treated according to an embodiment of the present invention. As previously mentioned, a principal reason for regurgitation associated with GERD is the mechanical failure of the deteriorated (or reflux appearance) gastroesophageal flap of the GEFV to close and seal against the higher pressure in the stomach. Due to reasons including lifestyle, a Grade I normal gastroesophageal flap of the GEFV may deteriorate into a Grade III deteriorated gastroesophageal flap. The anatomical results of the deterioration include moving a portion of the esophagus 41 that includes the gastroesophageal junction 52 and LES (not shown) toward the mouth through the hiatus 63 into the chest to create the hiatal hernia 61. This greatly reshapes the anatomy aboral of the gastroesophageal junction 52 and forms a flattened fundus 46.

Dr. Hill and colleagues developed a grading system to describe the appearance of the GEFV and the likelihood that a patient will experience chronic acid reflux. L. D. Hill, et al., *The gastroesophageal flap valve: in vitro and in vivo observations*, Gastrointestinal Endoscopy 1996:44:541-547. Under Dr. Hill's grading system, the normal movable flap 50 of the GEFV 49 illustrated in FIG. 1 is a Grade I flap valve that is the least likely to experience reflux. The deteriorated gastroesophageal flap 55 of the GEFV 49 illustrated in FIG. 2 is a Grade IV flap valve. The Grade IV flap valve is the most likely to experience reflux. Grades II and III reflect intermediate grades of deterioration and, as in the case of III, a high likelihood of experiencing reflux. With the deteriorated GEFV represented by deteriorated gastroesophageal flap 55 and the fundus 46 moved inferior, the stomach contents are presented a funnel-like opening directing the contents into the esophagus 41 and the greatest likelihood of experiencing reflux. Disclosed subsequently is a device, assembly, and method which may be employed to advantage according to an embodiment of the invention to treat the hiatal hernia 61 and restore the normal gastroesophageal flap valve anatomy.

Referring now to FIG. 3, it shows a device 100 according to an embodiment of the present invention. The device 100 includes a longitudinal member 102 for transoral placement of the device 100 into the stomach. The device further includes a first member 104, hereinafter referred to as the chassis, and a second member 106, hereinafter referred to as the bail. The chassis 104 and bail are hingedly coupled at 107. The chassis 104 and bail 106 form a tissue shaper which, as described subsequently in accordance with this embodiment of the present invention, shapes tissue of the stomach into the flap of a restored gastroesophageal flap valve. The chassis 104 and bail 106 are carried at the distal end of the longitudinal member 102 for placement in the stomach.

The device 100 has a longitudinal passage 101 to permit an endoscope 110 to be guided through the device and into the stomach. This permits the endoscope to service as a guide for guiding the device 100 through the patient's throat, down the esophagus, and into the stomach. It also permits the gastroesophageal flap valve restoration procedure to be viewed at each stage of the procedure.

As will be seen subsequently, to facilitate shaping of the stomach tissue, the stomach tissue is drawn in between the chassis 104 and the bail 106. Further, to enable a flap of sufficient length to be formed to function as the flap of a gastroesophageal flap valve, the stomach tissue is pulled down so that the fold line is substantially juxtaposed to the opening of the esophagus into the stomach. Hence, as will be seen, the stomach is first gripped at a point out and away from the esophagus and the grip point is pulled to almost the hinged connection 107 of the chassis 104 and bail 106. As described in copending application Ser. No. 11/001,666, filed Nov. 30, 2004, entitled FLEXIBLE TRANSORAL ENDOSCOPIC GASTROESOPHAGEAL FLAP VALVE RESTORATION DEVICE AND METHOD, which application is incorporated herein by reference, the device 100 is fed down the esophagus with the bail 106 substantially in line with the chassis 104. To negotiate the bend of the throat, and as described in the aforementioned referenced application, the chassis 104 and bail 106 are rendered flexible. The chassis 104 is rendered flexible by the slots 108 and the bail 106 is rendered flexible by the hingedly coupled links 112. Further details concerning the flexibility of the chassis 104 and the bail 106 may be found in the aforementioned referenced application.

As further shown in FIG. 3, the device further includes a tissue gripper 114. The gripper 114, in this embodiment, comprises a helical coil 115. The coil 115 is carried at the end of a cable 116 and may be attached to the end of the cable or be formed from the cable. In this embodiment, the helical coil 115 is attached to the cable 116 and is preceded by a guide 118 whose function will be described subsequently.

The helical coil 115 is shown in an approximate position to engage the stomach tissue out and away from the opening of the esophagus to the stomach. The helical coil 115 is guided into position by a guide structure 120 carried on the bail 106. The guide structure 120 comprises a guide tube 122. When the device 100 is first introduced down the esophagus into the stomach, the helical coil 115 is caused to reside well within the guide tube 122 to preclude the helical coil from accidentally or inadvertently snagging esophageal or stomach tissue.

The guide tube includes a longitudinal slit 126 having a circuitous configuration. The slit 126 permits the end of the cable to release or disassociate from the bail after the stomach tissue is gripped. The circuitous configuration of the slit 126 assures confinement of the cable 116 within the guide tube 122 until release of the cable is desired. The proximal end of the slit 126 has an enlarged portion or opening (not shown). This opening permits the cable and helical coil to reenter the lumen when the device 100 is readied for a repeated stomach tissue shaping procedure. To that end, the guide 118 has a conical surface that serves to guide the cable end back into the opening of the slit 126.

With continued reference to FIG. 3, the device 100 further comprises a fastener deployer 140. The fastener deployer includes at least one fastener deployment guide 142. The fastener deployment guide 142 takes the form of a guide lumen. Although only one guide lumen 142 is shown, it will be appreciated that the device 100 may include a plurality of such lumens without departing from the invention. The guide lumen terminates at a delivery point 144 where a fastener is driven from the device 100 and into, for example, the molded stomach tissue. The fastener deployer may also be used, according to an embodiment, to secure the stomach to the diaphragm.

The device 100 further includes a window 130 within the chassis 104. The window is formed of a transparent or semi-transparent material. This permits gastroesophageal anatomy, and more importantly the gastroesophageal junction (Z-line) to be viewed with the endoscope 110. The window includes a location marker 132 which has a know position relative to the fastener delivery point 144. Hence, by aligning the marker with a known anatomical structure, the fastener will be delivered a known distance from or at a location having a predetermined relation to the marker. For example, by aligning the marker with the Z-line, it will be know that the fastener will be placed aboral of the Z-line and that serosa tissue will be fastened to serosa tissue. As previously mentioned, this has many attendant benefits.

It may also be mentioned at this point that the device 100 further includes an invaginator 145 including a plurality of orifices 146. These orifices 146, which alternatively may be employed on the longitudinal member 102, are used to pull a vacuum to cause the device 100 to grip the inner wall surface of the esophagus. This will serve to stabilize the esophagus and maintain device positioning during the procedure. This vacuum gripping of the esophagus may also be used to particular advantage in the treatment of a hiatal hernia. Upon being thus gripped, the esophagus may be moved downwardly with the device toward the stomach to pull the stomach to within the diaphragm to eliminate the hiatal hernia.

Figure 4:
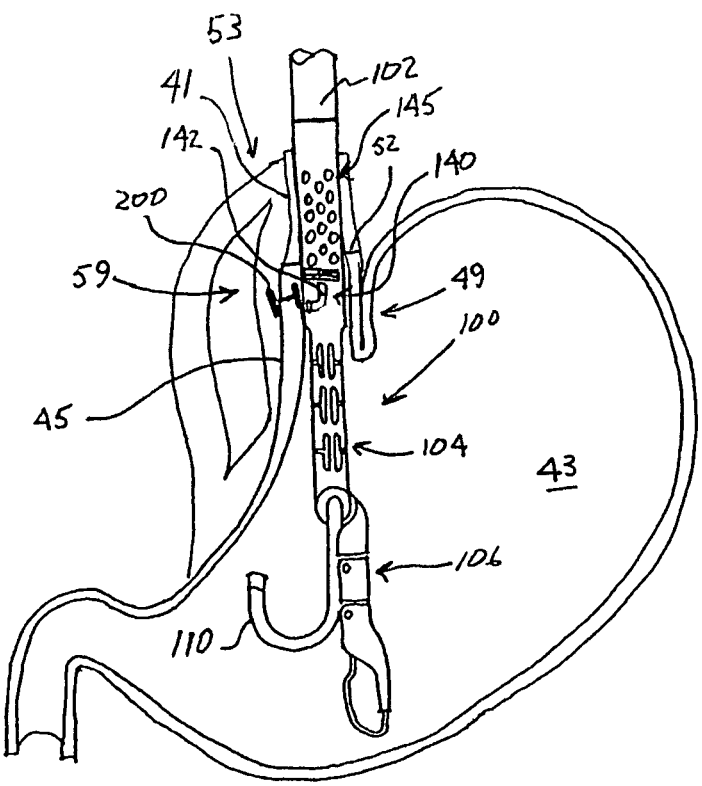
FIG. 4 is a side view of the apparatus of FIG. 3 securing the stomach to the diaphragm according to an embodiment of the invention.

Referring now to FIG. 4, it shows the device 100 in position to secure the stomach 43 to the diaphragm 53 following a successful restoration of a GEFV flap and/or to treat a hiatal hernia. More particularly, the device 100 of FIG. 4 is shown positioned in the stomach 43 by the elongated member 102. It is also rotated by about 180 degrees from its position shown in FIG. 3 to align the guide channel 142 with the lesser curve. This will enable the fastener deployer 140 to deploy at least one fastener 200 to secure the lesser curve 45 of the stomach 43 to the right crus 59 of the diaphragm 53. The endoscope 110 is positioned in the stomach 43 and brought to a reflexed view as illustrated so that it may look back on the device 100 for visualization of the procedure.

The invaginator 145 has vacuum gripped the sidewalls of the esophagus. This permits the device to be used for displacing the esophagus aborally towards the stomach for reducing the hiatal hernia. Preferably the esophagus is displaced sufficiently so that the stomach is behind or within the diaphragm 53. The esophagus is held in this position throughout the procedure.

Next, the fastener deployer deploys the at least one fastener 200 as illustrated. A deployment procedure for the application is described in greater detail herein after. The fastener is deployed to secure the lesser curve 45 of the stomach 43 to the right crus 59 of the diaphragm 53. Of course, in an actual procedure, a plurality of spaced fasteners would be deployed.

Once the fasteners are deployed, the device 100 is removed from the stomach 43. This may be accomplished by first aligning the bail 106 with the chassis 104 of the device 100. The endoscope may be used as a guide to guide the device out of the stomach and through the esophagus, throat, and mouth.

With the stomach thus secured to the diaphragm, the original anatomy is restored to correct the hiatal hernia. As will be noticed, this has been accomplished, according to this embodiment completely transorally without the need for any invasive surgical procedures.

Figure 5:
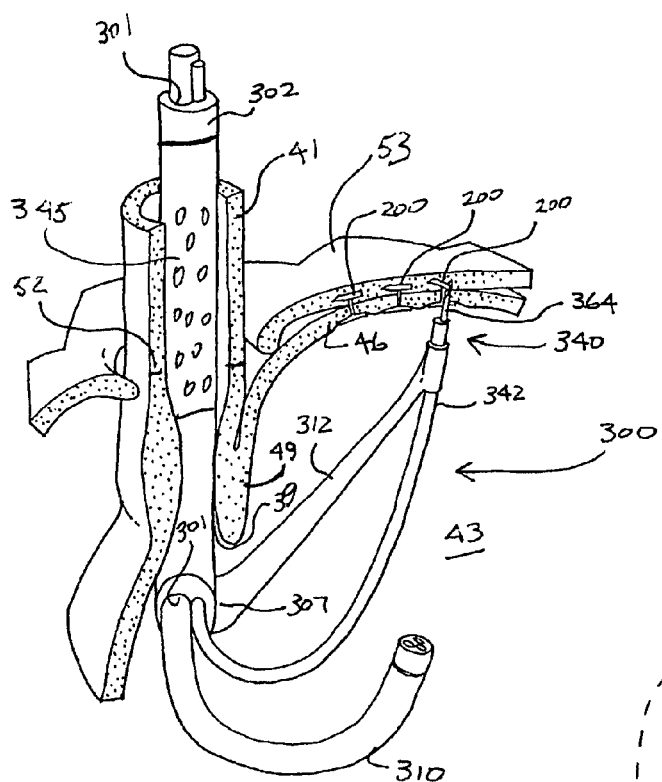
FIG. 5 is a perspective view, with portions cut away, of a device capable of securing the fundus of the stomach to the diaphragm according to another embodiment of the invention.

Referring now to FIG. 5, it shows another device 300 according to an embodiment of the invention for securing the stomach 43 to the diaphragm 53. Here, the fundus 46 of the stomach 43 is being secured to the diaphragm 53.

The device 300 may be employed for the restoration of a GEFV 49 and/or to treat a hiatal hernia. The device 300 is carried at the distal end of an elongated member 302 for being transorally placed in the stomach 43. It preferably includes an invaginator 345 of the type previously described for gripping the esophagus 41 and displacing it and the stomach aborally towards the diaphragm to reduce or eliminate the hiatal hernia. The invaginator may also be used to grip the esophagus during the restoration of the GEFV 49 after reduction of a hiatal hernia.

The device includes a support arm 312 that supports a fastener deployer 340 in close proximity to the fundus 46 of the stomach 43. The fastener deployer includes a guide tube 342 supported by the arm 312. The guide tube 342 guides the tissue piercing wire 364 and the fasteners 200 to the location where they are to be deployed. Again, a suitable deployment procedure and related deployment assembly are described herein after.

The device 300 further carries an endoscope 310. Again, the endoscope is positioned to enable visualization of the procedure. It is guided by a guide channel 301 in the elongated member 302.

The arm 312 is arranged for pivotal movement at 307 to enable proper positioning of the fastener deployer 340. To that end, it may be noted that the arm reaches outwardly to displace the fastener deployer 340 and the fasteners 200 spaced away from the esophageal opening 39 to the stomach 43.

Now that a device 100 according to an embodiment of the present invention and its use for treating a hiatal hernia has been described, a method of restoring the flap of a gastroesophageal flap valve according to this embodiment of the present invention will now also be described with reference to FIGS. 6-15. The procedure for restoring the flap of a gastroesophageal flap valve begins with loading a fastener or a plurality of fasteners into the device 100. As will be seen hereinafter, the fastener deployer includes a stylet, which guides each fastener into the tissue to be fastened. The process of loading a fastener, according to this embodiment, includes snapping a fastener onto the stylet. A representative fastener and stylet will be described subsequently with respect to FIGS. 16 and 17.

Figure 6:
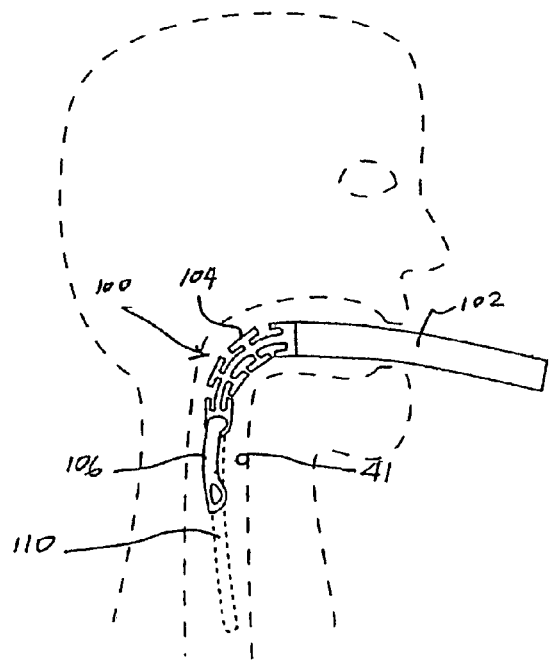
FIG. 6 is a simplified side view of an apparatus according to an embodiment of the invention being fed down an oral and esophageal passage of a patient.

Next, the bail 106 is moved to be substantially in line with the chassis 104. Next, the endoscope 110 is inserted into the device with an appropriate lubricant on the endoscope. Next, a bite block, of the type well known in the art, is inserted into the patient's mouth. A lubricant may be applied to the device and the device may now be inserted through the bite block in the subject's mouth. With the endoscope leading the device as illustrated in FIG. 6, the endoscope and device combination are fed down the esophagus 141 into the stomach. Of course, when the endoscope 110 reaches its fully inserted position, the device 100 may be further advanced on the endoscope utilizing the endoscope as a guide to within the stomach of the patient.

As previously mentioned, the device 100 is able to clear the bend in the patient's throat by virtue of being flexible as previously described. With the endoscope serving as a guide tube, very little force should be needed to get the device around the neck into the pharynx and down into the esophagus.

Figure 7:
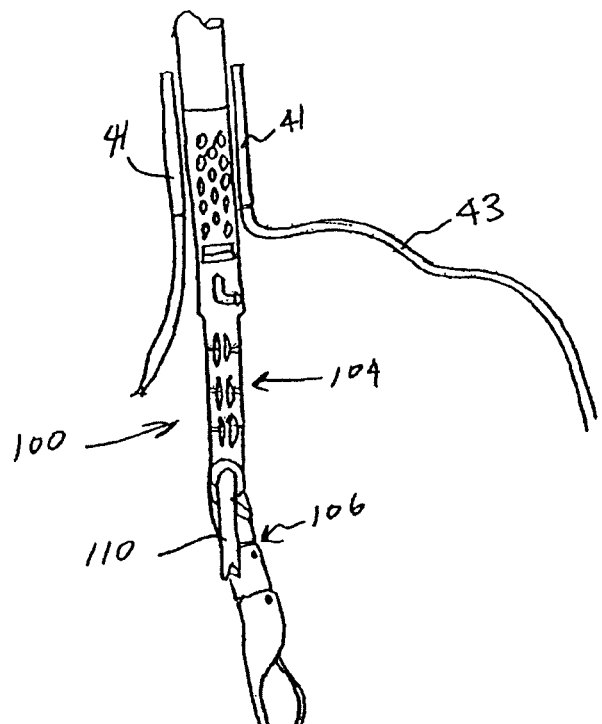
FIG. 7 is a side view, partly in cross-section, of a device according to an embodiment of the invention after having been initially fed into a stomach to initiate a GERD treatment procedure according to an embodiment of the invention.

FIG. 7 shows the device 100 upon reaching the interior of the stomach 43. Here it may be seen that the bail 106 is substantially in line with the chassis 104. The endoscope 110 remains within the device 100. Also in FIG. 7 it may be noted that the stomach is deflated. This is the normal condition of the stomach when the stomach is empty.

Figure 8:
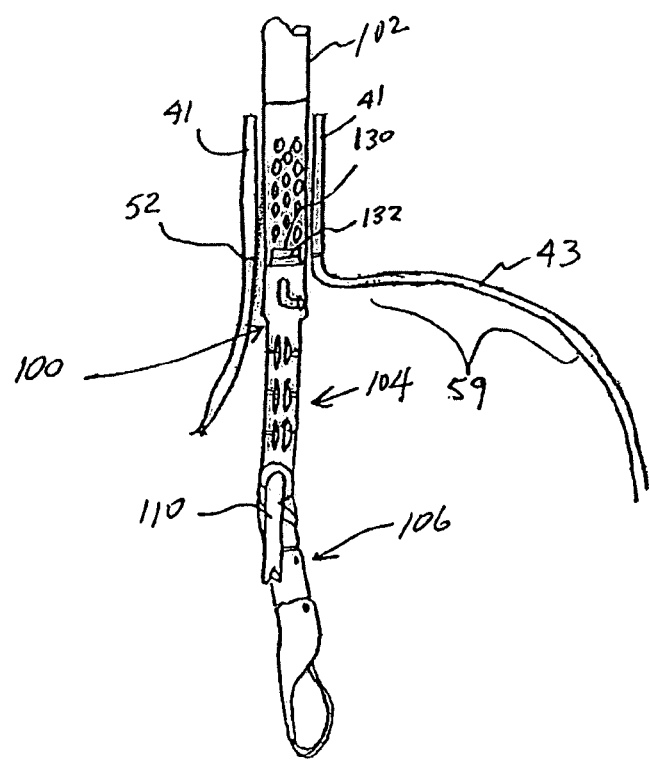
FIG. 8 is a view similar to FIG. 7 showing the device and stomach after the stomach has been inflated to a first pressure.

Once the device is positioned in the stomach as shown in FIG. 7, the stomach is inflated as shown in FIG. 8 by passing air through the endoscope into the stomach. The inflation of the stomach may be noted by the outward arcuate deflection of the stomach 43. The stomach should be inflated to a first pressure just sufficient to open the stomach and provide good visibility of gastric folds on the interior wall 59 of the stomach. Visualization of such gastric folds permits discernment of a proper point to grip the stomach for forming the gastroesophageal flap valve flap in a manner to be described hereinafter. Once the stomach has been inflated to the first pressure, the device is placed in a desired position relative to the Z-line by placing the marker of the window 130 in a desired position relative to the Z-line 52 marking the transition from the esophagus 41 to the stomach 43. In accordance with this embodiment, the marker 132 is aligned with the Z-line 52. In order to visualize the marker and the Z-line, the endoscope 110 is pulled back into the device 100 and more particular adjacent the marker 132 to visualize when the marker is aligned with the Z-line 52. With the marker 132 aligned with the Z-line 52, the distance from the marker 132 to a proximal point of the elongated member 102 relative to a rather fixed anatomy site of the patient, such as an incisor may be measured. This measurement may be marked on the elongated member 102 and later utilized for positioning the marker 132 adjacent the Z-line 52.

Figure 9:
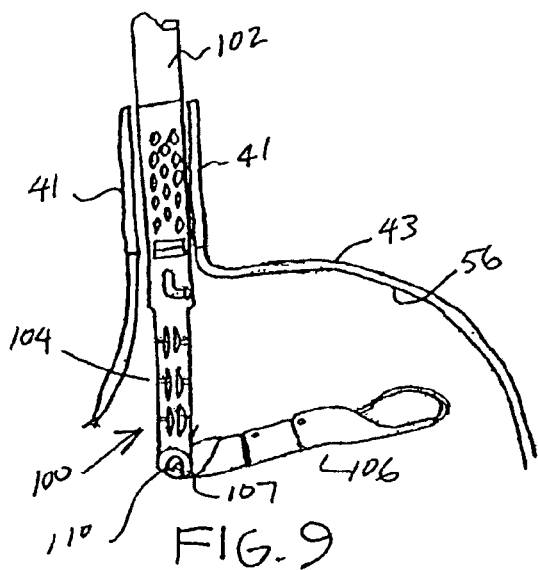
FIG. 9 is a view similar to FIG. 7 showing the device and stomach at a further stage of the procedure.

Referring now to FIG. 9, with the stomach still inflated to the first pressure, the endoscope is positioned inside the device just past the hinged connection 107 of the bail 106 and chassis 104. With the endoscope being located just past the hinged connection 107, the bail is then actuated to an approximally one-half closed position as illustrated. As the bail moves, the bail should be watched to make sure that it moves towards the greater curve 56 so it can move freely in the open space of the gastric cavity. With the endoscope in the position as shown in FIG. 9, the bail should be visible at all times.

Figure 10:
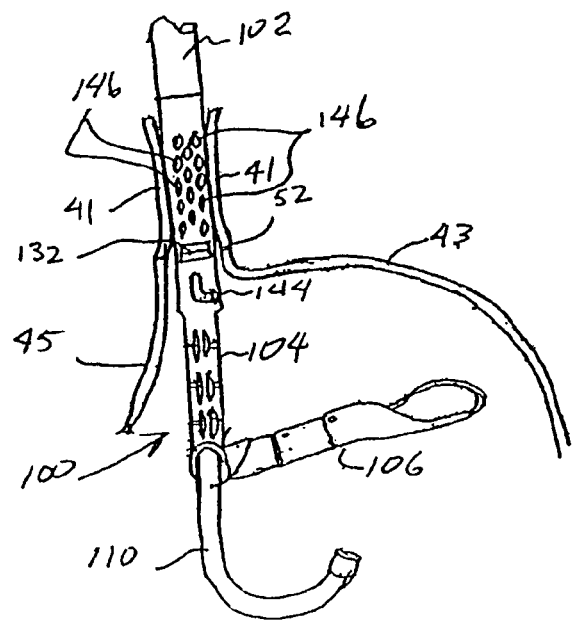
FIG. 10 is a view similar to FIG. 7 showing the device centered and gripping the esophagus.

Referring now to FIG. 10, the endoscope 110 is advanced back into the stomach 43 and brought to a reflexed view as illustrated so that it may look back on the device 100. With the operating end of the device in clear view, the device 100 is positioned in the center of the gastroesophageal flap valve to be formed where the posterior and anterior groove should be. This position is typically opposite the lesser curve 45.

Next, the device positioning relative to the Z-line 52 is checked to make sure that the marker 132 is in its desired position relative to the Z-line 52. In accordance with this embodiment, the marker 132 is placed adjacent or is aligned with the Z-line 52.

With the device in the correct starting position as shown in FIG. 10, a vacuum pump communicating with orifices 146 is energized to pull a vacuum through the orifices 146. This causes the orifices to engage the wall of the esophagus 41 for gripping the esophagus. As previously mentioned, this invagination permits the esophagus to be pushed into the stomach by distal movement of the elongated member 102 to treat a hiatal hernia and to stabilize the position of the device within the stomach. The vacuum is continued to be pulled through the orifices 146 until the vacuum is above the 50 kps mark on the vacuum pump. The device is then pushed gently aborally to reposition the esophagus to correct a hiatal hernia. It may be noted that this maneuver can also be used to visually check the position of the faster delivery point 144 relative to the Z-line. During this maneuver, the esophagus may roll back on itself and expose the esophageal Mucosa and the Z-line adjacent to the fastener delivery ports.

Figure 11:
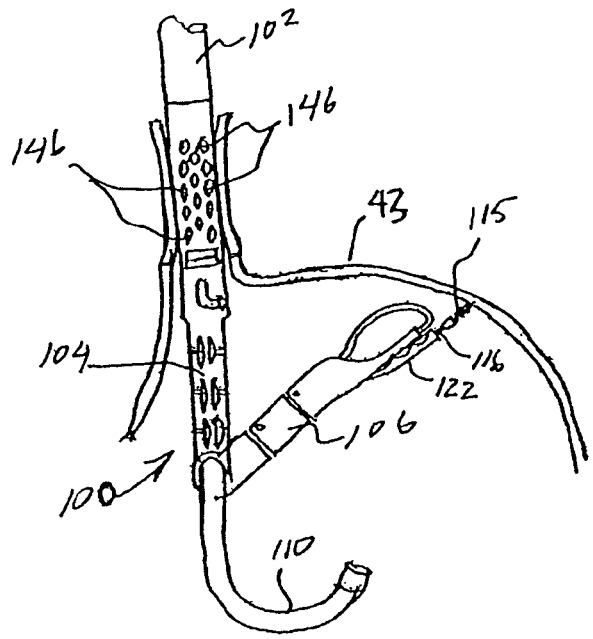
FIG. 11 is a view similar to FIG. 7 showing the device initially gripping the stomach tissue after the stomach has been reinflated to a second, higher pressure.

Referring now to FIG. 11, with the device locked in position by the vacuum orifices 146, the area in which the helical coil is to be engaged may be identified. The gripping location may be largely determined by the size or length of the flap to be restored of the restored gastroesophageal flap valve. This of course may differ from one patient to another depending on the severity of the hiatal hernia and the degree of valve degradation. Once the gripping location is selected, the stomach 43 is inflated to a second and higher pressure. The inflation pressure of the stomach is increased to the second and higher pressure so that the Mucosa appears tight and the folds essentially flatten. With the correct gripping spot identified, the bail 106 is moved to position the tip of a helical coil 115 at the correct gripping spot. Next, the device 100 is gently pulled upwardly or orally until the bail contacts the tissue at the desired gripping spot. Next, the helix 115 is advanced by the pushing of the cable 116 until the helix pushes into the Mucosa. Next, the cable 116 is turned to likewise turn the helix 115 in a clockwise direction to screw the helix into the tissue. As the cable is turned, some wind-up may be filled in the helix drive cable.

Figure 12:
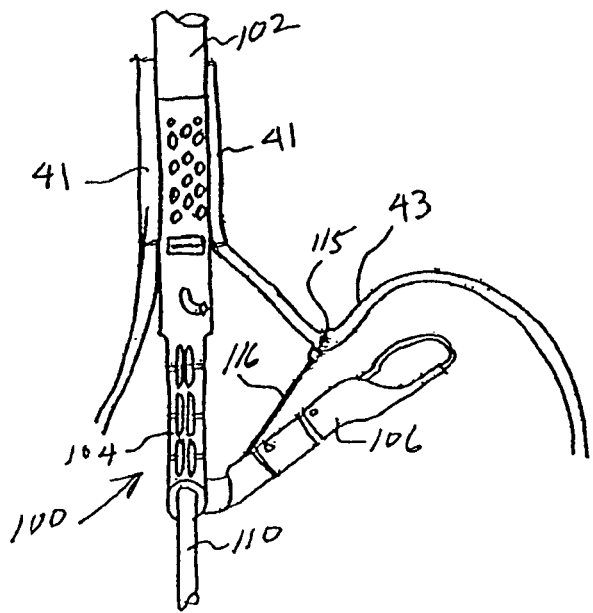
FIG. 12 is a view similar to FIG. 7 showing the stomach partially deflated and gripped stomach tissue being pulled aborally towards the device.

With the helical coil 115 firmly seated in the tissue, the wind-up in the cable 116 is released. Referring now to FIG. 12, with the retractor firmly seated in the tissue, the device 100 may be advanced slightly orally while at the same time the bail 116 may be opened slightly. This releases the cable 116 from the guide tube which has now been pulled back into the bail 106. The cable 116 exits the guide tube 122 (FIG. 3) by slipping through the circuitous slit 126. This operation is more particularly described in the aforementioned U.S. patent application Ser. No. 11/061,318, filed Feb. 18, 2005, incorporated herein by reference. Also at this time, the correct positioning of the device relative to the Z-line may be verified.

With the bail 106 slightly opened and the helix 115 engaged with the tissue 43, the interior of the stomach is now deflated through the endoscope 110. The stomach should be deflated such that the tissue appears loose and collapsed with the Mucosa folds being prominent. However, enough room should be left to view the device.

Figure 13:
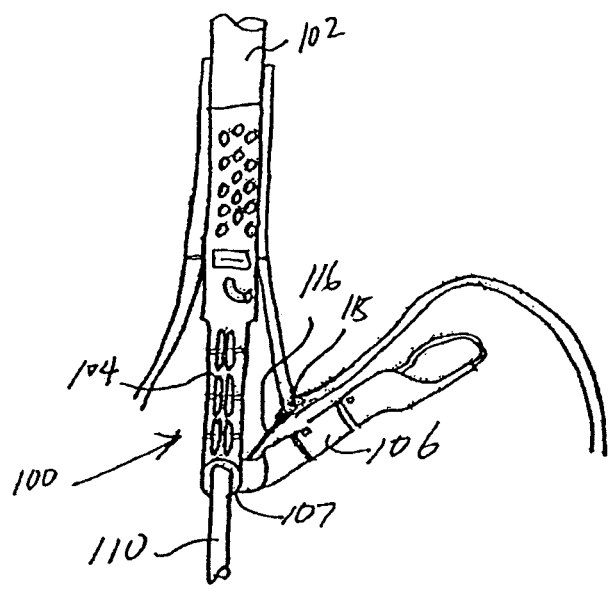
FIG. 13 is a view similar to FIG. 7 showing the gripped stomach tissue being pulled to almost within the device.
Figure 14:
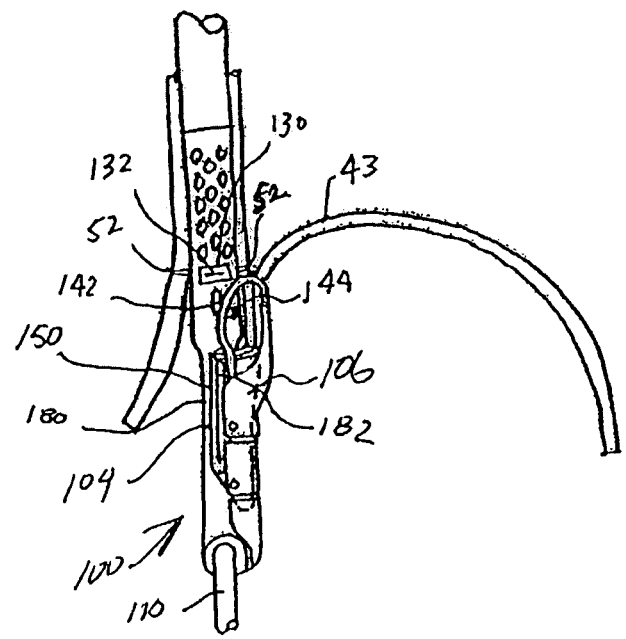
FIG. 14 is a view similar to FIG. 7 showing the gripped stomach tissue within the device, being molded, and ready to receive a fastener.

Referring now to FIG. 13, the gastric tissue is now gently pulled with the helix 115 and cable 116 towards the hinged connection 107 and the valve mold to be formed by the chassis 104 and closing bail 106. Once the helix is fully retracted into the bail 116, it is locked in place. The bail 106 may now be closed and the device and anatomy will appear as shown in FIG. 14. Here it will be noted that the stomach tissue aboral of the Z-line 52 is confined between the bail 106 and chassis 104 to create a fold 150. The fold is also adjacent the fastener delivery point 144 at the end of the fastener guide lumen. Since the fastener deployment point 144 is a known predetermined distance from the marker 132 of the window 130, and since the marker 132 is aligned with the Z-line 52, when a fastener is delivered from the fastener deployer of the device, the fastener will exit the fastener delivery point 144 at a point known to be aboral of the Z-line 52. This assures that only serosa tissue is being adhered to serosa tissue in the fixation of the stomach tissue in creating the flap 150. The flap 150 comprises layers 180 and 182 of stomach tissue.

With the tissue layers 180 and 182 now disposed within the mold of the chassis 104 and bail 106, the bail 106 may now be locked with respect to the chassis 104. It is now time to fasten the tissue layers 180 and 182 together by ejecting a fastener from the fastener deployer lumen 142 through the flap 150 from the fastener delivery point 144. The fastener thus deployed will serve to maintain the restored GEFV and the reduced hiatal hernia.

Before a fastener is ejected from the fastener deployer lumen 142, the stomach is once again inflated through the endoscope 110. The stomach is inflated to a point where one has a good view of the tissue fold and bail 106.

Figure 15:
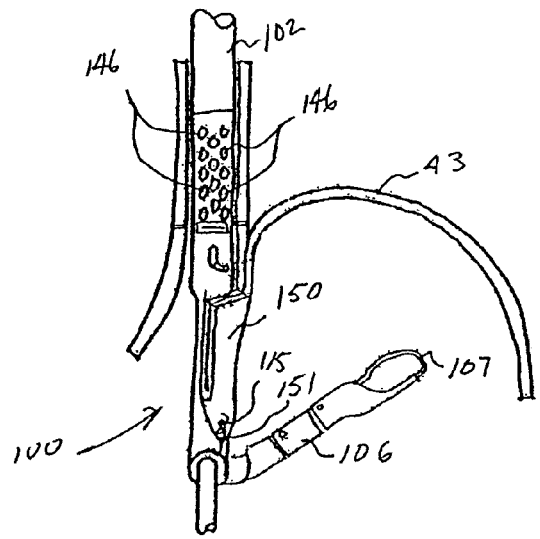
FIG. 15 is a view similar to FIG. 7 showing the molded stomach tissue after receiving a fastener.
Figure 16:
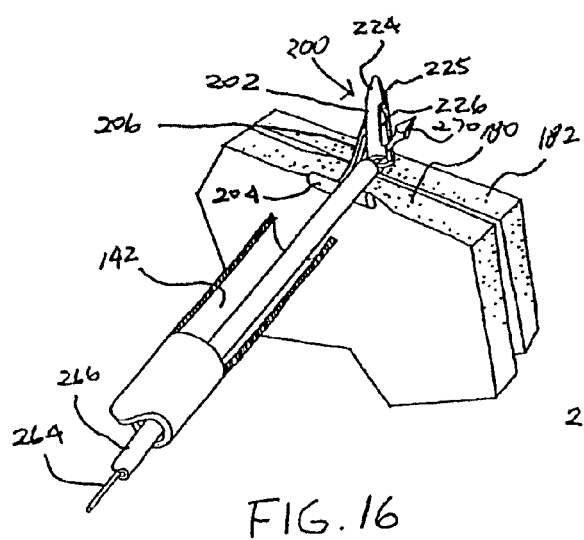
FIG. 16 is a perspective view illustrating a manner in which the devices of FIGS. 3 and 5 may deploy a fastener for securing the stomach to the diaphragm, for example.
Figure 17:
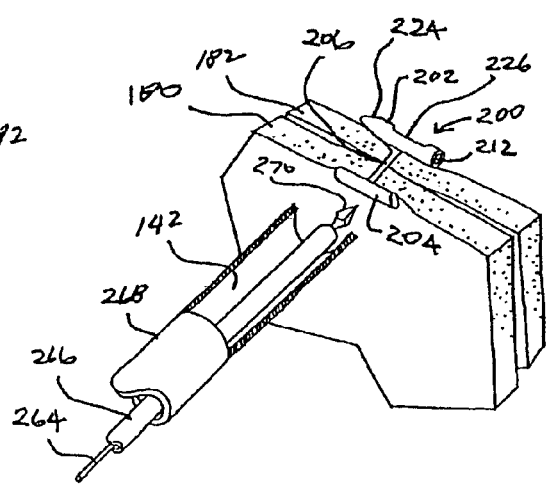
FIG. 17 is a perspective view showing a fastener fully deployed.

FIGS. 16 and 17 illustrate a manner in which the fasteners 200 may be deployed to fasten tissue layers 180 and 182. The tissue layers 180 and 182 are meant to be merely representative of any tissue layers which may be fastened together, whether they be stomach tissue layers from forming a flap or stomach and diaphragm tissue layers fastened to secure the stomach to the diaphragm. The fastener 200 generally includes a first member 202, a second member 204, and a connecting member 206. As may be noted in FIG. 15, the first member 202 and second member 204 are substantially parallel to each other and substantially perpendicular to the connecting member 206 which connects the first member 202 to the second member 204.

The first member 202 is generally cylindrical or can any shape. It has a channel 212 that extends therethrough. The though channel 112 is dimensioned to be slidingly received on a tissue piercing deployment wire 264.

The first member 202 includes a pointed tip 224. The tip 224 may be conical and more particularly takes the shape of a truncated cone. The tip can also be shaped to have a cutting edge in order to reduce tissue resistance.

The first member 202 also has a continuous lengthwise slit 225. The slit 225 includes an optional slot 226 that communicates with the through channel 212. The slot 226 has a transverse dimension for more readily enabling receipt of the tissue piercing deployment wire 264 during deployment of the fastener 200. Also, because the fastener member 202 is formed of flexible material, the slit 225 may be made larger through separation to allow the deployment wire to be snapped into and released from the through channel 212.

In addition to the fastener 200 and the deployment wire 264, the assembly shown in FIGS. 16 and 17 further includes a pusher 266 and a guide tube 268. The subassembly of the tissue piercing wire 264, fastener 200, and pusher 266 may be guided to its intended location relative to the tissue layers 180 and 182 by the guide tube 268. The tissue piercing wire 264, fastener 200, and the pusher 266 are all initially within the guide tube 268. The guide tube 268 is representative of the fastener deployment guide and to that end, includes the fastener deployment guide lumen 142. The subassembly of the tissue piercing wire 264, fastener 200, and pusher 266 may be guided to its intended location relative to the tissue layers 180 and 182 by the guide lumen 142.

As shown in FIGS. 16 and 17, the tissue piercing wire 264 has a tip 270 helping it pierce the tissue layers 180 and 182 that will form the restored gastroesophageal flap valve flap 150. The pusher 266 has pushed the first member 202 of the fastener 200 through the tissue layers 180 and 182 on the tissue piercing wire 264. This may be accomplished by moving the wire 264 and the pusher 266 together.

As may be further noted in FIG. 16, the first member 202 is clearing the wire 264 and tissue layer 182. The tissue piercing wire 264 may now be retracted into the pusher 266 and the tissue piercing wire 264 and pusher 266 may be withdrawn.

FIG. 17 illustrates the fastener 200 in its fully deployed position. It will be noted that the fastener has returned to its original shape. The tissue layers 180 and 182 are fastened together between the first member 202 of the fastener 200 and the second member 204 of the fastener 200. The connecting member 206 extends through the tissue layers 180 and 182.

In accordance with a further method of utilizing the fastener deployment assembly of FIGS. 16 and 17, the tissue piercing wire 264 may be first advanced through the tissue layers 180 and 182 by a full stroke and then locked. The tip 270 of the deployment wire 264 should extend through the bail 206 with minimal tenting of the tissue. Next, the pusher 266 is advanced. Visual confirmation that the first fastener member 202 is through the tissue is then made. In doing so, the very distal end of the pusher 266 may be visible when the first member 202 of the fastener 200 is fully deployed. Next, while holding the pusher 266 at the last noted position, the tissue piercing wire 264 is retracted. The first member 202 of the fastener 200 will fall to the side when the tissue piercing wire 264 reaches the pusher 266. When the tissue piercing wire 264 reaches the pusher 266 and after the fastener 200 is deployed, the pusher 266 is pulled back with the tissue piercing wire. If additional fastener deployment guides are provided, the foregoing steps for deploying a fastener such as fastener 200 may be repeated.

With the fasteners successfully deployed, the vacuum pull through orifices 146 may now be turned off to release the device from the esophagus wall as illustrated in FIG. 15. At this time, the bail 106 of the device 100 may be slightly opened and the helical coil 115 may be released from the stomach tissue. As may be seen in FIG. 15, the procedure just described results in a flap 150 to be formed. At this time, an additional fastener or fasteners may be loaded onto the tissue piercing deployment wire 264 at the proximal end of the longitudinal member 102.

To render the flap uniform about the opening of the orifice into the stomach, it is necessary at this time to rotate the device 102 and repeat the previously described procedure for forming a further flap portion. Before this is done, however, it is desirable to position the bail 106 to an almost closed position. Then, the device 100 is moved aborally further into the stomach until the tip end 107 of the bail 106 comes to rest on the tip 151 of the newly formed flap portion. This is the location where the helical coil 115 will next engage the stomach tissue for molding and fixating as previously described.

The foregoing is repeated until a complete valve flap is formed. When the appearance of the valve flap is satisfactory as viewed through the endoscope for visual confirmation, the helical coil 115 is reloaded back into its original position with the device 100. The vacuum suction through orifices 146 is turned off to release the wall of the esophagus from the device. The bail 106 is then moved to a fully opened position as seen, for example, in FIG. 7. The endoscope may now be retracted along with the stylet and pusher controls. With the retraction of the foregoing verified, the stomach may now be deflated and the device 100 may be removed from the stomach and esophagus. This then completes the GEFV restoration procedure according to this embodiment of the invention.

While particular embodiments of the present invention have been shown and described, modifications may be made, and it is thereto intended in the appended claims to cover all such changes and modifications which fall within the true spirit and scope of the invention.

What is claimed is:

1. A method for securing the stomach to the diaphragm and for restoring a gastroesophogeal flap valve, comprising:
   selecting a first portion of a stomach tissue of a patient;
   restoring a gastroesophageal valve using the first portion of the stomach tissue, the first portion of the stomach tissue forming an intersection between the esophagus and the stomach;
   providing a tissue fastening device having a fastener, the fastener having a first member and a second member, the first member having a tissue piercing pointed tip;
   advancing the tissue fastening device down the throat of the patient;
   securing a second portion of stomach tissue, the second portion of tissue being a portion of the stomach separate from the first portion of tissue and being a portion of the greater curvature spaced apart from an esophageal opening, the securing step being carried out after restoring the gastroesophageal valve during the restoring step;
   advancing a tissue piercing deployment wire through the first portion of tissue and through the second portion of tissue and locking the tissue piercing deployment wire in place;
   using a pusher, advancing the fastener over the tissue piercing deployment wire extending through a channel in the first member and inserting the tissue piercing pointed tip of the first member through the first portion of tissue and the second portion of tissue; and withdrawing the tissue piercing deployment wire from the channel through a lengthwise slit extending the entire length of the first member in order to deploy the first member through the second portion of tissue.

2. The method of claim 1, further comprising the step of:
inflating the stomach before the selecting step.

\* \* \* \* \*